United States Patent [19]
Levitt et al.

[11] Patent Number: 4,470,014
[45] Date of Patent: Sep. 4, 1984

[54] NMR SPECTROSCOPY

[75] Inventors: Malcolm H. Levitt, Hull; Thomas A. Frenkiel, Oxford, both of England

[73] Assignee: National Research Development Corporation, London, England

[21] Appl. No.: 408,281

[22] Filed: Aug. 16, 1982

[30] Foreign Application Priority Data

Mar. 26, 1982 [GB] United Kingdom ................ 8208928

[51] Int. Cl.$^3$ ............................................ G01R 33/08
[52] U.S. Cl. .................................... 324/311; 324/307
[58] Field of Search ............... 324/300, 307, 308, 310, 324/311, 312, 313, 314

[56] References Cited

PUBLICATIONS

U. Haeberlen and J. S. Waugh, Coherent Averaging Effects in Magnetic Resonance, Physical Review, vol. 175, No. 2, Nov. 10, 1968, pp. 453-467.

J. B. Grutzner and R. E. Santini, Coherent Broad-Band Decoupling-an Alternative to Proton Noise Decoupling in Carbon-13 Nuclear Magnetic Resonance Spectroscopy, Journal of Magnetic Resonance, vol. 19, pp. 173-187 (1975).

R. Freeman, S. P. Kempsell, and M. H. Levitt, Radiofrequency Pulse Sequences which Compensate their Own Imperfections, Journal of Magnetic Resonance, vol. 38, pp. 453-479 (1980).

M. H. Levitt, R. Freeman, Composite Pulse Decoupling, Journal of Magnetic Resonance, vol. 43, pp. 502-507 (1981).

M. H. Levitt, R. Freeman, T. Frenkiel, Broadband Heteronuclear Decoupling (Communications), Journal of Magnetic Resonance, vol. 47, pp. 328-330 (1982).

Primary Examiner—Michael J. Tokar
Attorney, Agent, or Firm—Cushman, Darby & Cushman

[57] ABSTRACT

In a method of heteronuclear decoupling in high resolution pulsed NMR spectroscopy, during acquisition of signals emanating from a nuclear species to be observed (e.g. carbon-13), irradiation of an interfering nuclear species (e.g. protons) is effected by means of a train of composite pulses, each of which approximately inverts the longitudinal magnetization. The pulses are of two types respectively having opposite r.f. phases, and the train constitutes a repeated sequence which consists of $2^{N+1}$ pulses of each type (where N is a positive integer) and which has a form chosen in accordance with specific rules to ensure effective decoupling.

6 Claims, 3 Drawing Figures

NMR SPECTROSCOPY

This invention relates to methods of heteronuclear decoupling in high resolution pulsed nuclear magnetic resonance (NMR) spectroscopy of the kind in which, during the acquisition from a sample of signals resulting from resonance of a nuclear species to be observed, the sample is irradiated with radio frequency energy substantially at the resonant frequency of an interfering nuclear species (commonly protons).

In U.S. patent application Ser. No. 382,648, filed May 27, 1982 by Malcolm H. Levitt, now Pat. No. 4,443,761, and in a paper by Levitt and Freeman published in J. Magn.Reson., Vol. 43, page 502 (1981), there are disclosed methods of this kind in which the irradiation is in the form of a train of composite pulses each of which is effective to cause at least approximate inversion of the longitudinal magnetisation in respect of the interfering nuclear species, the composite pulses being of two types which differ only by virtue of the r.f. phase for one type being opposite that for the other type. The term 'composite pulse' is used herein in the same sense as in the documents referred to above and in the paper by Freeman et al published in J. Magn.Reson., Vol. 38, page 453 (1980), and refers to a pulse sequence (which may include at least one period of free precession between individual pulses) whose constituent pulses are associated in the sense that the state of the relevant nuclear spins is of interest only when the sequence has been completed. It should be noted that the reference to a train of such pulses is not intended to imply that there is necessarily an interval between successive composite pulses; indeed for the purposes of methods of the kind under consideration it will normally be desirable for there to be no significant delay between successive composite pulses of the train. The term 'longitudinal' refers to the direction of the static magnetic field used in the NMR technique, about which the unperturbed spins of the interfering nuclear species precess.

As noted in the Patent Application referred to above, one suitable form of composite pulse consists of three constituent pulses with negligible intervals between them, the first and third pulses having the same r.f. phase and each being of nominal duration $\pi/2\gamma B_2$, and the second pulse having a r.f. phase which differs by 90° from that of the first and third pulses and having a nominal duration between $\pi/\gamma B_2$ and $3\pi/2\gamma B_2$, where $B_2$ is the magnetic flux density associated with the r.f. irradiation and $\gamma$ is the gyromagnetic ratio for the interfering nuclear species; in conventional notation this form of composite pulse may be denoted by $90°(X)\alpha(Y)90°(X)$, where has a value between 180° and 270° and X and Y refer to orthogonal directions perpendicular to the direction of the static magnetic field (in a reference frame rotating about the last mentioned direction). This form of composite pulse is effective to achieve population inversion of the interfering nuclear spins in a manner which is relatively insensitive to resonance frequency offsets as compared with the use of a simple 180° pulse. The length of the second pulse (given by the angle $\alpha$) may be chosen according to the desired bandwidth of inversion relative to the irradiating field strength, which is conveniently expressed in units of frequency in accordance with the quantity $\gamma B_2/2\pi$. Thus where $\alpha$ has a value of 180° the relative effective bandwidth is about $2(\gamma B_2/2\pi)$, whereas it is only about half of this where $\alpha$ has a value of 240°; over this narrower offset range, however, the inversion is more accurate than in the case where $\alpha$ has the lower value.

As noted above, in the methods under consideration use is made of two types of composite pulse which differ only by virtue of the r.f. phase for one type being opposite that for the other type. Conveniently the two types of composite pulse may be denoted respectively by R and $\bar{R}$; for example if R has the form $90°(X)\alpha(Y)90°(X)$ then $\bar{R}$ will have the form $90°(-X)\alpha(-Y)90°(-X)$. In order to achieve the desired decoupling effect, however, it is not sufficient for the two types of pulse to occur at random in the train of composite pulses. In particular the Patent Application and paper by Levitt and Freeman referred to above explain, on the basis of average Hamiltonian theory, the efficacy of using a train in the form of a repeated sequence which consists of two pulses of each type and which involves less than three changes of type between successive pulses. The specific sequences which satisfy this definition may be denoted $RR\bar{R}\bar{R}$, $R\bar{R}\bar{R}R$, $\bar{R}RR\bar{R}$, and $\bar{R}\bar{R}RR$; these four sequences are equivalent in effect, as will readily be appreciated when it is noted that the four types of train respectively formed by repeating them differ only at the beginning and end of the train. To put the matter in another way, the four sequences are related to each other by the operation of cyclic permutation, which may in the present case be defined as the transfer of at least one pulse from the end to the beginning of a sequence, with the order of the transferred pulses preserved in cases where the transfer involves more than one pulse; it is to be understood that in the most general sense cyclic permutation includes the case where the number of transferred pulses is equal to the number of pulses in the sequence, in which case the permuted sequence is the same as the unpermuted sequence. It may also be noted that the sequences $RR\bar{R}\bar{R}$ and $\bar{R}\bar{R}RR$ are related to each other by the operation of interchanging the two types of pulse R and $\bar{R}$ (which is equivalent to inversion of the r.f. phase for the whole sequence), and likewise for the sequences $R\bar{R}\bar{R}R$ and $\bar{R}RR\bar{R}$; it will be evident that two sequences related to each other in this way are equivalent in effect, since the allocation of the symbols R and $\bar{R}$ between the two types of pulse is arbitrary.

As will be explained more fully below, the present invention is based on the realisation that improved results can be obtained by using, instead of one of the four-pulse sequences discussed, a more complex sequence which is appropriately related to one of those sequences.

According to the invention there is provided a method of heteronuclear decoupling in high resolution pulsed NMR spectroscopy in which, during the acquisition from a sample of signals resulting from resonance of a nuclear species to be observed, the sample is irradiated with radio frequency energy substantially at the resonant frequency of an interfering nuclear species, the irradiation being in the form of a train of composite pulses each of which is effective to cause at least approximate inversion of the longitudinal magnetisation in respect of said interfering nuclear species, said composite pulses being of two types which differ only by virtue of the r.f. phase for one type being opposite that for the other type and said train being in the form of a repeated sequence consisting of $2^{N+1}$ pulses of each type, where N is a positive integer, said sequence being derivable by a logical expansion process from a basic sequence which consists of two pulses of each type and which involves less than three changes of type between successive pulses, said expansion process consisting of at least one step of deriving a higher order sequence from a lower order sequence so that said higher order sequence is a cyclic permutation of a composite sequence which consists of M different sub-sequences, where M is an even number not greater than four, each of said sub-sequences being related to said lower order sequence by a relationship selected from (a) the cyclic permutation of an even number of pulses, (b) the cyclic permutation of an odd number of pulses, (c) the cyclic permutation of an even number of pulses combined with the interchange of the two types of pulse, and (d) the cyclic permutation of an odd number of pulses combined with the interchange of the two types of pulse, with the selection being subject to the conditions that:

(A) if M is four then the four types of relationship (a), (b), (c) and (d) respectively apply to the four sub-sequences constituting said composite sequence, and (B) if M is two then the four types of relationship (a), (b), (c) and (d) respectively apply to the four sub-sequences constituting a notional sequence composed of said composite sequence and a composite sequence of a similar kind which is related to said composite sequence by the cyclic permutation of an even number of pulses.

If desired, the train of composite pulses may also be applied during the period immediately prior to the excitation of resonance of the nuclear species to be observed, in order to establish a wide-band Overhauser enhancement.

The theoretical basis of the invention is highly complex, and will therefore be presented here only in outline. As for the previous work, the operation of the relevant sequences of composite pulses can be expressed in terms of average Hamiltonian theory—see the paper by Haeberlen and Waugh published in Phys.Rev., Vol. 175, page 453 (1968). As to this, it suffices here to note that in considering the interaction between the respective spins of the nuclear species to be observed and the interfering nuclear species, in the presence of a periodic perturbation of the latter spins with a sufficiently rapid repetition rate one can replace the true interaction Hamiltonian by an average Hamiltonian (denoted $\overline{H}$); $\overline{H}$ is composed of an infinite series of terms which progressively decrease in importance if the repetition rate is rapid enough. Where the periodic perturbation corresponds to a sequence of composite pulses, it is found that these terms are easily calculated only if it is assumed that the composite pulses achieve exact inversion of the interfering spins. In practice this is not the case, since no composite pulse will operate perfectly over a wide range of resonance frequency offsets. This consideration is particularly significant in cases where the composite pulse R has a nominal form 90° (X)180° (Y)90° (X); as indicated above, although the effective bandwidth is large for this type of pulse, inversion is by no means exact over the full range.

It is therefore appropriate to consider the possibility of improving decoupling by using sequences which will compensate for imperfections in the effects of the individual composite pulses. For this purpose it is convenient to assume that the imperfection in the inversion is quantified by a small parameter $\delta$ and to expand each of the terms in the average Hamiltonian as a power series in $\delta$; these series will also rapidly converge if $\delta$ is small.

In this way one can express the average Hamiltonian $\overline{H}$ as a sort of matrix as follows:

$$\begin{aligned}
\overline{H} = &\ \overline{H}_0(\delta^0) + \overline{H}_0(\delta^1) + \overline{H}_0(\delta^2) + \ldots \\
&+ \overline{H}_1(\delta^0) + \overline{H}_1(\delta^1) + \overline{H}_1(\delta^2) + \ldots \\
&+ \overline{H}_2(\delta^0) + \overline{H}_2(\delta^1) + \overline{H}_2(\delta^2) + \ldots \\
&+ \qquad\quad + \qquad\quad + \\
&\ \ \cdot \qquad\qquad \cdot \qquad\qquad \cdot \\
&\ \ \cdot \qquad\qquad \cdot \qquad\qquad \cdot \\
&\ \ \cdot \qquad\qquad \cdot \qquad\qquad \cdot
\end{aligned}$$

Under suitable conditions this will converge towards the right and the bottom. In order to improve the decoupling performance the aim is to make as many terms as possible of this matrix disappear. The use of the four-pulse sequences, such as $RR\overline{R}\overline{R}$, referred to above in fact results in cancellation of only the top left term in this matrix. It is therefore clear that considerable scope for improvement exists.

The key feature in the present case is the development of a set of rules which enable one to construct sequences that can be expected to be more effective in respect of the decoupling performance than the basic four-pulse sequences such as $RR\overline{R}\overline{R}$. In order to present these rules in a general form it is appropriate firstly to set out some definitions. We denote by C any sequence which consists of K composite pulses of type R and K composite pulses of type $\overline{R}$. Then P denotes a set of K sequences which are related to C by the cyclic permutation of an odd number of pulses, and Q denotes a set of K sequences which are related to C by the cyclic permutation of an even number of pulses (including the case where this even number is 2K). $\overline{P}$ denotes a set of K sequences which are derived from P by the interchange of the two types of pulse, and $\overline{Q}$ denotes a set of K sequences which are derived from Q in the same way. It will be appreciated that all the members of these four sets are sequences each consisting of K composite pulses of type R and K composite pulses of type $\overline{R}$. As an illustration, if C is $RR\overline{R}\overline{R}$, then P consists of $\overline{R}RR\overline{R}$ and $R\overline{R}\overline{R}R$, Q consists of $\overline{R}\overline{R}RR$ and $RR\overline{R}\overline{R}$, $\overline{P}$ consists of $R\overline{R}\overline{R}R$ and $\overline{R}RR\overline{R}$ (and hence is identical to P), and $\overline{Q}$ consists of $RR\overline{R}\overline{R}$ and $\overline{R}\overline{R}RR$ (and hence is identical to Q).

It can be shown that, for any given form of C, all members of the sets P,Q,$\overline{P}$ and $\overline{Q}$ are of equivalent effect to C when repeated to form trains of pulses. It is, however, possible to combine members of different ones of these sets in such a way as to produce an expanded sequence E which can be used in place of C to improve the decoupling performance. In order to achieve this improvement, it is necessary in the general case to combine (in any order) four sequences respectively selected from the sets P,Q,$\overline{P}$ and $\overline{Q}$. The resultant composite sequence E can be shown to have the following properties when considered in relation to the matrix expansion of $\overline{H}$ set out above:

(a) If C is such that in a particular row of the matrix the terms up to the (m)th are all zero, then E will be such that the same is true and at least the (m+1)th term in that row will also be zero.

(b) If C is such that for each column of the matrix up to the (m)th the terms in that column up to the (n)th are all zero, then E will be such that the same is true and at least the (n+1)th term in each of the relevant columns will also be zero.

As an example, consider again the case where C is RRRR̄, for which only the term H̄$_o$($\delta^0$) is zero. In this case the use of an appropriate expanded sequence E such as RRRR̄ R̄R̄R̄R R̄R̄R̄R RRRR̄ (which is representative of the class denoted by QPQ̄P) would result in at least the terms H$_o$($\delta^1$) and H$_1$($\delta^0$) also being zero; in fact, as will appear more fully below, the use of this 16-pulse expanded sequence gives better results than the minimum indicated here. It will be noted that in setting out the exemplary sequence E gaps have been left between the successive sub-sequences derived from the sequence C; it is emphasised that this convention in the notation has been adopted (both here and elsewhere in the description) solely for ease of comprehension, and is not intended to imply that in practice there would be any significant intervals between the sub-sequences.

The general condition indicated above requires that in order to obtain an improvement in performance over that obtainable with a given sequence C the expanded sequence E must consist of a total of 8K composite pulses. In many cases, however, a degree of improvement can be obtained with an expanded sequence E consisting of only 4K composite pulses. This possibility arises because in such cases two parts of the general fourfold expansion are redundant. Two simple cases in which this applies are as follows:

(a) If members of Q are the same as members of Q̄ or P̄, then an expansion of the form QP or PQ is sufficient to achieve one stage of improvement over C.

(b) If members of Q are the same as members of P or P̄, then an expansion of the form QQ̄ or Q̄Q is sufficient to achieve one stage of improvement over C.

More general conditions for redundancy may be stated as follows:

(1) If there is a representative of either QP or PQ which is related to a representative of either Q̄P or P̄Q by the cyclic permutation of an even number of pulses, than an expansion of the form QP and PQ is sufficient.

(2) If there is a representative of either QP̄ or P̄Q which is related to a representative of either Q̄P or PQ̄ by the cyclic permutation of an even number of pulses, then an expansion of the form QP̄ or P̄Q is sufficient.

(3) If there is a representative of either QQ̄ or Q̄Q which is related to a representative of either PP̄ or P̄P by the cyclic permutation of an even number of pulses, then an expansion of the form QQ̄ or Q̄Q is sufficient. It will be seen that in all these cases a suitable expanded sequence E will consist of two sub-sequences respectively selected from two of the four sets P,Q,P̄ and Q̄, and will be related by the cyclic permutation of an even number of pulses to a sequence of a similar kind for which the two sub-sequences are respectively selected from the other two of the four sets.

It will be appreciated that any particular expanded sequence E derived by means of the foregoing rules can be replaced with equivalent effect by a sequence related to E by cyclic permutation and/or interchange of the two types of composite pulse. It will further be appreciated that any particular expanded sequence E can itself be treated as the starting sequence C for a further step of expansion in accordance with the foregoing rules; in theory, the expansion process can be continued indefinitely, with successive improvements in performance associated with the respective stages of expansion.

This may be illustrated yet again by considering the case where one starts with C in the form of the basic sequence RRRR̄. In this case Q=Q̄, so that an expansion of the form QP is sufficient to achieve a degree of improvement over C in decoupling performance. The expanded sequence E may then take the form RRRR̄ R̄R̄R̄R; with this form, both the terms H̄$_o$($\delta^1$) and H̄$_1$($\delta^0$), in addition to the term H̄$_o$($\delta^0$), will be zero. For the next step of the expansion process, if one takes C to be of the form RRRR̄ R̄R̄R̄R then neither of the simple redundancy conditions (a) and (b) is satisfied and one must have regard to the more general conditions (1) to (3). Considering condition (3) in particular, a representative of QQ̄ is RRRR̄ R̄R̄R̄R R̄R̄R̄R RRRR̄ and a representative of P̄P is R̄R̄R̄R RRRR̄ RRRR̄ R̄R̄R̄R. These two are related by the cyclic permutation of four pulses, so that an expansion of the form QQ̄ is sufficient. Accordingly for the 16-pulse sequence RRRR̄ R̄R̄R̄R R̄R̄R̄R RRRR̄ the terms H̄($\delta^2$), H̄$_1$($\delta^1$) and H̄$_2$($\delta^0$) will additionally be zero. The same is of course true of cyclic permutations of this sequence, such as RRRR̄ R̄R̄R̄R R̄R̄R̄R RRRR̄. It will be noted, however, that the last mentioned sequence cannot be regarded, as can the 16-pulse sequence from which it is derived, as simply made up of the four types of basic sequence which consist of two pulses of each type and involve less than three changes of type between successive pulses. The expansion process can of course be carried on from the 16-pulse stage, leading for example to 64-pulse sequences such as RRRR̄ R̄R̄R̄R R̄R̄R̄R RRRR̄ RRRR̄ R̄R̄R̄R R̄R̄R̄R RRRR̄ R̄R̄R̄R RRRR̄ RRRR̄ R̄R̄R̄R RRRR̄ R̄R̄R̄R R̄R̄R̄R RRRR̄ , for which H̄$_j$($\delta^k$) will be zero for all values of (j+k) not greater than four.

In the illustrative exposition set out in the preceding paragraph, each step in the expansion process leading to the 64-pulse sequence involves a doubling of the length of the relevant sequence, since account is taken in each case of one of the redundancy conditions. It may be noted, however, that one can also regard the quoted 64-pulse sequence as a fourfold expansion (of the form QPQ̄P) of the 16-pulse sequence RRRR̄ R̄R̄R̄R R̄R̄R̄R RRRR̄, which (as indicated above) can itself be regarded as a like expansion of the basic sequence RRRR̄.

Although the expansion process could in theory be extended indefinitely to sequences of even higher orders, other factors (which are not taken into account in the foregoing discussion but are considered further below) are likely to restrict the practical utility of very long sequences, and it is thought that few cases will arise in practice in which it would be advantageous to use sequences of more than 64 pulses.

In the foregoing discussion reference is made to the repetition rate of the periodic perturbation of the interfering spins. As noted in the paper by Levitt and Freeman referred to above, the theory in respect of the four-pulse sequences such as RRRR̄ is based on the assumption that $2\pi JT << 1$, where T is the total duration of the sequence and J is the spin coupling constant (expressed in frequency units). A similar consideration applies in respect of the expanded sequences discussed above, with T being the duration of the basic four-pulse sequence from which the expanded sequence is derived (and not the total duration of the expanded sequence itself).

The invention will be further discussed, and examples of how it may be performed will be described, with reference to the accompanying drawings, in which.

In the following description it is assumed for the sake of definiteness that the nuclear species to be observed is carbon-13, with protons constituting the interfering nuclear species.

Figure 1:
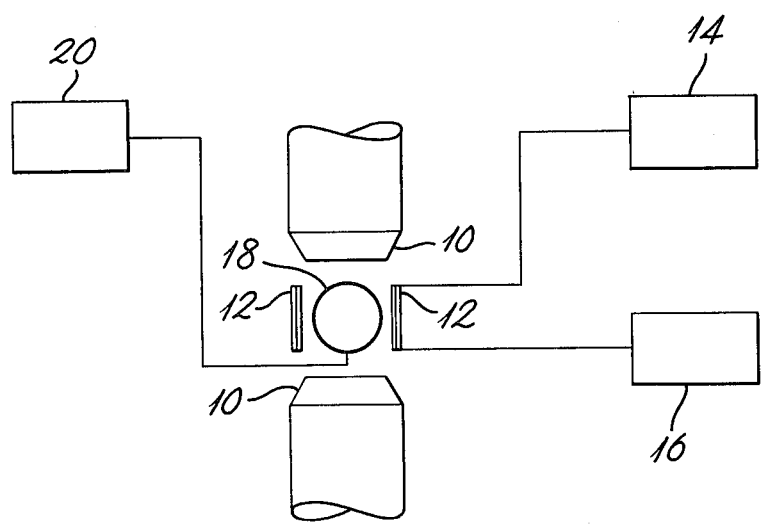
FIG. 1 is a diagrammatic representation of a spectrometer which may be used in practising the invention.

Referring to FIG. 1, a sample (not shown) containing these species is placed in a region of substantially uniform magnetic field $B_o$ which is produced between a pair of pole pieces 10. A pair of coils 12 arranged on an axis perpendicular to the direction of field $B_o$ receives r.f. pulses from a transmitter 14 to produce the required field $B_1$ for excitation of $^{13}C$ resonance. The transmitter 14 contains gating and delay elements for the control of duration and relative phase of the r.f. pulses. The coils 12 also serve to pick up the free induction decay signals from the sample, these signals being fed to a receiver 16 in which they are coherently detected, the detected signals being sampled to provide data from which the $^{13}C$ spectrum can be derived by conventional Fourier transformation. A further coil 18, which is shown for convenience as having an axis perpendicular to both $B_o$ and $B_1$, is used to produce a proton decoupling field $B_2$. The coil 18 is energised by a transmitter 20 having similar control facilities to those of the transmitter 14. For a field $B_o$ of about 4.7 tesla the proton decoupling transmitter frequency occupies a band near 200 MHz while the $^{13}C$ excitation frequency of the transmitter 14 is near 50 MHz. The required decoupling bandwidth depends on the chemical shifts which are present in the sample material and on the strength of field $B_o$, but typically a bandwidth of several kHz will be appropriate when $B_o$ has the value quoted above.

The transmitter 20 generates a continuous wave signal whose phase is changed at intervals (between levels of relative phase 0°, 90°, 180° and 270°) in a repetitive pattern such that the output of the transmitter 20 constitutes a train of composite pulses with negligible intervals between them. The composite pulses are of two types R and $\bar{R}$, respectively having the nominal forms 90° (X)α(Y)90° (X) and 90° (−X)α(−Y) 90° (−X) with α equal to either 180° or 240°, and the repetitive pattern of phase changes is chosen so as to correspond to one of the expanded sequences discussed above and derived from the basic sequence RR$\bar{R}\bar{R}$, for example the 16-pulse sequence RR$\bar{R}\bar{R}$ $\bar{R}\bar{R}$RR $\bar{R}\bar{R}$RR RR$\bar{R}\bar{R}$ . It will be appreciated that the actual duration of each composite pulse (and hence the repetition period for a sequence with a given number of such pulses) will vary inversely in accordance with the value chosen for the strength of the decoupling field $B_2$. For instance, where this value corresponds to about eight kHz when expressed in units of frequency the duration of a composite pulse of the form 90° (X)180° (Y)90° (X) will be about 0.125 millisecond, so that the repetition period for a 16-pulse sequence will be about two milliseconds. In some cases, however, it may be desired to use low decoupling powers, corresponding say to a value for the field strength as low as one kHz; for this value, the corresponding figures would be about one millisecond for the duration of the composite pulse and 16 milliseconds for the repetition period of the 16-pulse sequence. In such cases one is particularly likely to wish to use a value of 180° rather than 240° for the angle α, in order to obtain the benefit of the greater effective bandwidth for the decoupling. By way of comparison it may be noted here that, in order to obtain a complete $^{13}C$ spectrum, it will normally be necessary for the intervals at which the free induction decay signals are sampled to be no greater than about 0.1 millisecond when the field $B_o$ has a value of 4.7 tesla.

The transmitter 20 is of course switched on throughout the period during which data are being acquired from the signals resulting from the $^{13}C$ resonance excited by a pulse from the transmitter 14. As a further contribution to sensitivity, the transmitter 20 may also be switched on during the period immediately prior to this pulse to provide nuclear Overhauser enhancement.

Figure 2:
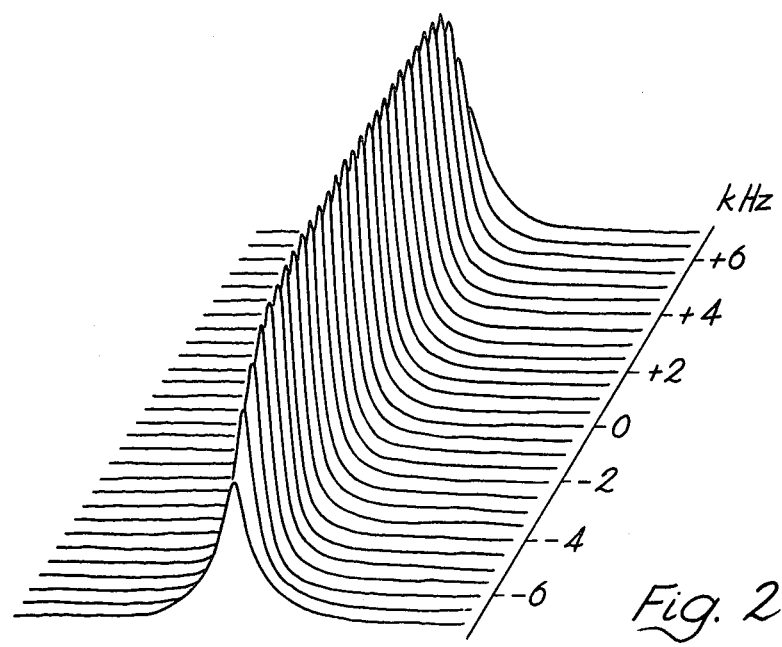
FIG. 2 is a diagram illustrating the results obtained by means of a method according to the invention.
Figure 3:
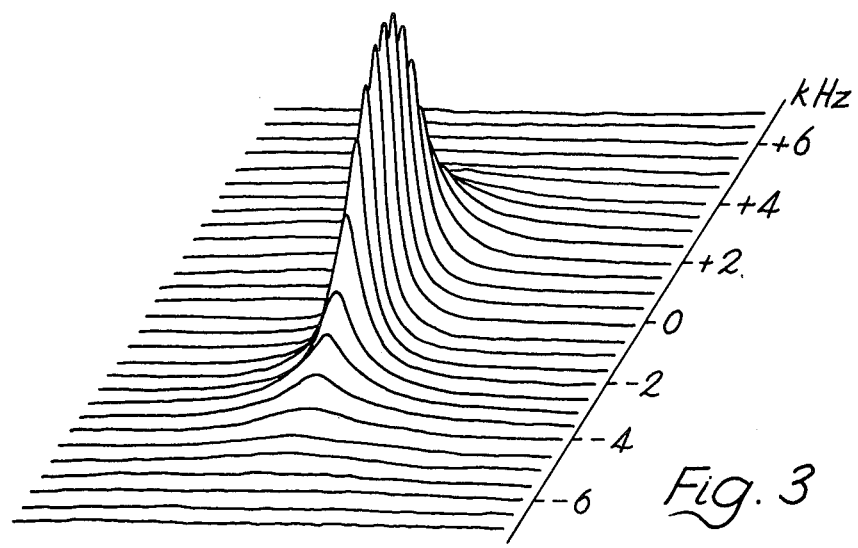
FIG. 3 is a diagram illustrating results in a comparable experiment using a known method of heteronuclear decoupling.

FIG. 2 illustrates results which have been obtained using an arrangement such as just discussed, the sample material being dimethyl carbonate with the field $B_o$ having a value of 4.7 tesla, the strength of the decoupling field $B_2$ corresponding to 8.3 kHz, the angle α for the composite pulses being 240°, and the pulse sequence having the form RR$\bar{R}\bar{R}$ $\bar{R}\bar{R}$RR $\bar{R}\bar{R}$RR RR$\bar{R}\bar{R}$ . FIG. 3 illustrates results obtained using a similar arrangement, but replacing the decoupling method of the present invention by a known method employing square-wave phase modulation, as disclosed in the paper by Grutzner and Santini published in J. Magn.Reson., Vol. 19, page 173 (1975). In both cases the observed carbon 13 signals are plotted as a function of proton resonance offset, the spectral width displayed being 40 Hz. It will be seen that the broad band decoupling performance is much superior in the case of FIG. 2, for which the peak heights remain within five percent of that observed for coherent on-resonance decoupling over a range of more than ±five kHz.

It is appropriate finally to consider certain factors which may have a bearing on the choice of particular cases of the length of the sequence (in terms of the number of composite pulses in the sequence). Where it is possible to use a relatively high decoupling power, it will normally be possible to obtain the required effective bandwidth for decoupling when using composite pulses with α equal to 240°, and this value will then normally be preferred to 180° since it gives more perfect inversion for each composite pulse over the relevant frequency range. In such cases (which are of course exemplified by the arrangement used to obtain the results illustrated in FIG. 2), although the use of a 16-pulse sequence offers a considerable improvement in performance over the use of a basic four-pulse sequence, the theoretical improvement that could be achieved by going to even longer sequence is much less significant. The main sphere of application of such very long sequences is thus more likely to arise in cases where one wishes to use composite pulses with α equal to 180°, particularly with a view to obtaining an appropriate effective bandwidth while using a low decoupling power.

The theoretical advantages of using very long sequences must, however, be balanced against certain practical considerations which are likely to be particularly cogent where a low decoupling power is used. The theoretical treatment of the effect of the relevant sequences of composite pulses shows that at the end of a sequence the state of the interfering nuclear spins is as if the coupling between them and the nuclear spins to be observed were much reduced, and the greater the length of the sequence the closer this reduced interaction approaches zero. In practice, however, it is desirable that decoupling should be as good as possible within the duration of the sequence. One reason for this is the requirement noted above for sampling the free induction decay signals at a rate which is appreciably greater than the sequence repetition rate even when using the shorter sequences and relatively high decoupling powers. This necessitates the acquisition of data at instants within, and not merely at the end of, each sequence, which results in the generation of artefacts in the spectrum; the intensity of these will be weak if the decoupling is good throughout. A further reason is that a number of irreversible processes can interfere with the compensation effected by the sequence, examples being spin relaxation and molecular diffusion; the main relaxation process involved will probably be proton transverse relaxation, which in typical samples has a time constant in the range of about 0.1–1 second. Such irreversible processes have the effect of increasing the width of the decoupled spectral line at the expense of its height.

Both the consideration relating to sampling and that relating to irreversible processes become more significant the greater is the actual duration of the sequence, which of course means that for a given number of pulses in the sequence they become more serious the lower is the decoupling power. Moreover, the second consideration becomes particularly significant for sequences consisting of more than 16 composite pulses. This arises because, in following the rules for constructing the expanded sequences, while one can construct a 16-pulse sequence entirely from four-pulse sub-sequences which in themselves have good decoupling performance, the same is not true for 32-pulse or higher order sequences.

Taking these factors into account, one can conclude that in general the use of an appropriate 16-pulse sequence should always give better results than are obtainable when using four-pulse or eight-pulse sequences, but that the use of longer sequences may not in all cases result in improvement in the overall performance.

This may be illustrated by reference to experimental observations carried out on one particular sample using composite pulses with $\alpha$ equal to 180°. With a strength of the decoupling field $B_2$ corresponding to eight kHz, it was found that a dramatic improvement in decoupling performance was obtained by using a 16-pulse sequence in place of a basic four-pulse sequence, and that the use of sequences consisting of 32, 64, 128 and 256 pulses offered further small improvements. At a field strength corresponding to 1.5 kHz, however, the 64-pulse sequence was found to give a performance marginally better than that obtained with 16-pulse or 256-pulse sequences, while at a field strength corresponding to one kHz the best overall decoupling performance was achieved when using a 16-pulse sequence.

We claim:

1. A method of heteronuclear decoupling in high resolution pulsed NMR spectroscopy, in which during the acquisition from a sample of signals resulting from resonance of a nuclear species to be observed the sample is irradiated with radio frequency energy substantially at the resonant frequency of an interfering nuclear species, the irradiation being in the form of a train of composite pulses each of which is effective to cause at least approximate inversion of the longitudinal magnetisation in respect of said interfering nuclear species, said composite pulses being of two types which differ only by virtue of the r.f. phase for one type being opposite that for the other type and said train being in the form of a repeated sequence consisting of $2^{N+1}$ pulses of each type, where N is a positive integer, said sequence being derivable by a logical expansion process from a basic sequence which consists of two pulses of each type and which involves less than three changes of type between successive pulses, said expansion process consisting of at least one step of deriving a higher order sequence from a lower order sequence so that said higher order sequence is a cyclic permutation of a composite sequence which consists of M different sub-sequences, where M is an even number not greater than four, each of said sub-sequences being related to said lower order sequence by a relationship selected from (a) the cyclic permutation of an even number of pulses, (b) the cyclic permutation of an odd number of pulses, (c) the cyclic permutation of an even number of pulses combined with the interchange of the two types of pulse, and (d) the cyclic permutation of an odd number of pulses combined with the interchange of the two types of pulse, with the selection being subject to the conditions that:

(A) if M is four then the four types of relationship (a), (b), (c) and (d) respectively apply to the four sub-sequences constituting said composite sequence, and (B) if M is two then the four types of relationship (a), (b), (c) and (d) respectively apply to the four sub-sequences constituting a notional sequence composed of said composite sequence and a composite sequence of a similar kind which is related to said composite sequence by the cyclic permutation of an even number of pulses.

2. A method according to claim 1, in which said expansion process consists of not more than four steps for each of which M is two, whereby N is equal to the number of said steps.

3. A method according to claim 2, in which N is two.

4. A method according to claim 3 in which said repeated sequence is constituted by four different successive sub-sequences each consisting of two pulses of each type and involving less than three changes of type between successive pulses.

5. A method according to claim 1, 2, 3 or 4, in which each of said composite pulses consists of three constituent pulses with negligible intervals between them, the first and third constituent pulses having the same r.f. phase and each being of nominal duration $\pi/2\gamma B_2$, and the second constituent pulse having a r.f. phase which differs by 90° from that of the first and third constituent pulses and having a nominal duration between $\pi/\gamma B_2$ and $3\pi/2\gamma B_2$, where $B_2$ is the magnetic flux density associated with the r.f. irradiation and $\gamma$ is the gyromagnetic ratio for said interfering nuclear species.

6. A method according to claim 5, in which the nominal duration of said second constituent pulse is $4\pi/3\gamma B_2$.

* * * * *